US010314714B2

(12) United States Patent
Hibri et al.

(10) Patent No.: US 10,314,714 B2
(45) Date of Patent: Jun. 11, 2019

(54) PERCUTANEOUS IMPLANTABLE NUCLEAR PROSTHESIS

(71) Applicant: Spinal Stabilization Technologies LLC, San Antonio, TX (US)

(72) Inventors: Nadi S. Hibri, San Antonio, TX (US); James D. Lutz, San Antonio, TX (US)

(73) Assignee: SPINAL STABILIZATION TECHNOLOGIES LLC, San Antonio, TX (US)

( * ) Notice: Subject to any disclaimer, the term of this patent is extended or adjusted under 35 U.S.C. 154(b) by 560 days.

(21) Appl. No.: 14/932,242

(22) Filed: Nov. 4, 2015

(65) Prior Publication Data

US 2016/0120653 A1    May 5, 2016

Related U.S. Application Data

(60) Provisional application No. 62/074,925, filed on Nov. 4, 2014.

(51) Int. Cl.
*A61F 2/02* (2006.01)
*A61F 2/44* (2006.01)
(Continued)

(52) U.S. Cl.
CPC ............ *A61F 2/441* (2013.01); *A61F 2/3094* (2013.01); *A61F 2/442* (2013.01); *B29C 41/14* (2013.01);
(Continued)

(58) Field of Classification Search
CPC ........ A61F 2/3094; A61F 2/441; A61F 2/442; A61F 2002/444; A61F 2002/30092; A61F 2002/30235; B29C 41/14; B29C 45/14
See application file for complete search history.

(56) References Cited

U.S. PATENT DOCUMENTS 4,187,390 A    2/1980   Gore .................... 174/102 R
4,478,898 A    10/1984  Kato .................... 428/36.91
(Continued)

FOREIGN PATENT DOCUMENTS

CN    101448471    6/2009
CN    103099689    5/2013
(Continued)

OTHER PUBLICATIONS

International Search Report and Written Opinion for PCT/US2015/058976 dated Jan. 25, 2016.
(Continued)

*Primary Examiner* — Jacob J Cigna
*Assistant Examiner* — Lee A Holly
(74) *Attorney, Agent, or Firm* — Norton Rose Fulbright US LLP

(57) ABSTRACT

A multi-chamber balloon for a nuclear implant has an elastomeric membrane defining inner and outer chambers integral with a valve body. The valve body includes a core portion and sealing membrane for sealing the inner and outer chambers. An assembly for manufacturing the multi-chamber balloon includes a balloon mandrel which may be dip coated in a silicone dispersion to create an elastomeric membrane for the inner and outer chambers integral with the valve body. The elastomeric membrane formed on the mandrel is partially inverted to form a coaxial elastomeric structure with the smaller inner chamber disposed within the larger outer chamber. The valve is incorporated into the inner and outer chambers to form a unitary structure.

14 Claims, 9 Drawing Sheets

(51) Int. Cl.
  *B29C 45/14* (2006.01)
  *B29C 41/14* (2006.01)
  *A61F 2/30* (2006.01)

(52) U.S. Cl.
  CPC .... *B29C 45/14* (2013.01); *A61F 2002/30092* (2013.01); *A61F 2002/30235* (2013.01); *A61F 2002/30242* (2013.01); *A61F 2002/30586* (2013.01); *A61F 2002/444* (2013.01)

(56) References Cited

U.S. PATENT DOCUMENTS

| | | | |
|---|---|---|---|
| 4,619,641 A | 10/1986 | Schanzer | 604/8 |
| 4,743,480 A | 5/1988 | Campbell et al. | 428/36.5 |
| 5,152,782 A | 10/1992 | Kowligi et al. | 623/1.46 |
| 5,181,921 A | 1/1993 | Makita et al. | 606/195 |
| 5,192,310 A | 3/1993 | Herweck et al. | 623/1.27 |
| 5,466,509 A | 11/1995 | Kowligi et al. | 428/141 |
| 5,628,786 A | 5/1997 | Banas et al. | 623/1.13 |
| 5,827,327 A | 10/1998 | McHaney et al. | 623/1.44 |
| 5,860,425 A | 1/1999 | Benderev et al. | 128/898 |
| 5,865,845 A | 2/1999 | Thalgott | 623/17.16 |
| 5,879,366 A | 3/1999 | Shaw et al. | 606/213 |
| 5,888,220 A | 3/1999 | Felt | 128/898 |
| 5,888,226 A | 3/1999 | Rogozinski | 623/17.16 |
| 5,910,277 A | 6/1999 | Ishino et al. | 264/127 |
| 5,928,284 A | 7/1999 | Mehdizadeh | 623/17.13 |
| 5,935,147 A | 8/1999 | Kensey et al. | 606/213 |
| 5,954,767 A | 9/1999 | Pajotin et al. | 623/23.72 |
| 5,972,022 A | 10/1999 | Huxel | 606/215 |
| 5,976,174 A | 11/1999 | Ruiz | 606/213 |
| 6,001,125 A | 12/1999 | Golds et al. | 623/23.7 |
| 6,001,130 A | 12/1999 | Bryan et al. | 623/17.16 |
| 6,007,570 A | 12/1999 | Sharkey et al. | 607/96 |
| 6,007,575 A | 12/1999 | Samuels | 623/1.15 |
| 6,019,793 A | 2/2000 | Perren et al. | 623/17.16 |
| 6,036,724 A | 3/2000 | Lentz et al. | 623/1.1 |
| 6,126,682 A | 10/2000 | Sharkey et al. | 607/96 |
| 6,140,452 A | 10/2000 | Felt et al. | 528/60 |
| 6,146,419 A | 11/2000 | Eaton | 623/11.11 |
| 6,180,848 B1 | 1/2001 | Flament et al. | 623/11.11 |
| 6,183,518 B1 | 2/2001 | Ross et al. | 623/17.16 |
| 6,206,921 B1 | 3/2001 | Guagliano et al. | 606/92 |
| 6,224,630 B1 | 5/2001 | Bao et al. | 623/17.16 |
| 6,248,131 B1 | 6/2001 | Felt et al. | 623/17.12 |
| 6,344,054 B1 | 2/2002 | Parodi | 623/1.13 |
| 6,361,637 B2 | 3/2002 | Martin et al. | 156/187 |
| 6,398,803 B1 | 6/2002 | Layne et al. | 623/1.13 |
| 6,402,750 B1 | 6/2002 | Atkinson et al. | 606/279 |
| 6,419,704 B1 | 7/2002 | Ferree | 623/17.12 |
| 6,428,576 B1 | 8/2002 | Haldimann | 623/17.16 |
| 6,436,143 B1 | 8/2002 | Ross et al. | 623/17.16 |
| 6,443,988 B2 | 9/2002 | Felt et al. | 623/17.12 |
| 6,482,234 B1 | 11/2002 | Weber et al. | 623/17.12 |
| 6,527,804 B1 | 3/2003 | Gauchet et al. | 623/17.12 |
| 6,533,818 B1 | 3/2003 | Weber et al. | 623/17.12 |
| 6,582,466 B1 | 6/2003 | Gauchet | 623/17.11 |
| 6,645,248 B2 | 11/2003 | Casutt | 623/17.12 |
| 6,673,103 B1 | 1/2004 | Golds et al. | 623/1.13 |
| 6,712,853 B2 | 3/2004 | Kuslich | 623/17.16 |
| 6,733,533 B1 | 5/2004 | Lozier | 623/17.12 |
| 6,780,497 B1 | 8/2004 | Walter | 428/311.51 |
| 6,852,223 B2 | 2/2005 | Huang et al. | 210/500.36 |
| 6,893,465 B2 | 5/2005 | Huang | 623/17.12 |
| 6,893,466 B2 | 5/2005 | Trieu | 623/17.12 |
| 6,932,843 B2 | 8/2005 | Smith et al. | 623/17.11 |
| 6,936,070 B1 | 8/2005 | Muhanna | 623/17.12 |
| 6,958,077 B2 | 10/2005 | Suddaby | 623/17.11 |
| 6,969,405 B2 | 11/2005 | Suddaby | 623/17.12 |
| 7,001,431 B2 | 2/2006 | Bao et al. | 623/17.12 |
| 7,056,345 B2 | 6/2006 | Kuslich | 623/17.16 |
| 7,077,865 B2 | 7/2006 | Bao et al. | 623/17.12 |
| 7,156,861 B2 | 1/2007 | Scribner et al. | 606/192 |
| 7,156,877 B2 | 1/2007 | Lotz et al. | 623/17.16 |
| 7,220,282 B2 | 5/2007 | Kuslich | 623/17.16 |
| 7,273,497 B2 | 9/2007 | Ferree | 623/17.16 |
| 7,297,158 B2 | 11/2007 | Jensen | 623/1.44 |
| 7,556,650 B2 | 7/2009 | Collins et al. | 623/17.11 |
| 7,563,284 B2 | 7/2009 | Coppes et al. | 623/17.12 |
| 7,641,691 B2 | 1/2010 | Lotz et al. | 623/17.12 |
| 7,645,301 B2 | 1/2010 | Hudgins et al. | 623/17.12 |
| 7,713,301 B2 | 5/2010 | Bao et al. | 623/17.12 |
| 7,731,753 B2 | 6/2010 | Reo et al. | 623/17.13 |
| 7,766,965 B2 | 8/2010 | Bao et al. | 623/17.12 |
| 7,789,913 B2 | 9/2010 | Collins et al. | 623/17.12 |
| 7,799,079 B2 | 9/2010 | Hestad et al. | 623/17.12 |
| 7,837,733 B2 | 11/2010 | Collins et al. | 623/17.12 |
| 7,896,920 B2 | 3/2011 | Yuksel et al. | 623/17.16 |
| 7,931,689 B2 | 4/2011 | Hochschuler et al. | 623/17.12 |
| 7,947,079 B2 | 5/2011 | Helm et al. | 623/17.12 |
| 7,993,404 B2 | 8/2011 | Trieu | 623/17.12 |
| 7,998,210 B2 | 8/2011 | Edie et al. | 623/17.11 |
| 8,012,210 B2 | 9/2011 | Lin et al. | 623/17.12 |
| 8,012,211 B2 | 9/2011 | Kuslich | 623/17.12 |
| 8,043,381 B2 | 10/2011 | Hestad et al. | 623/17.16 |
| 8,083,800 B2 | 12/2011 | Edie | 623/17.16 |
| 8,092,536 B2 | 1/2012 | Ahrens et al. | 623/17.11 |
| 8,100,978 B2 | 1/2012 | Bass | 623/17.16 |
| 8,123,808 B2 | 2/2012 | Dewey et al. | 623/17.12 |
| 8,142,456 B2 * | 3/2012 | Rosqueta | A61B 17/12022 606/157 |
| 8,236,057 B2 | 8/2012 | Wirtel, III et al. | 623/17.12 |
| 8,246,682 B2 | 8/2012 | Slivka et al. | 623/17.11 |
| 8,287,595 B2 | 10/2012 | Vresilovic et al. | 623/17.12 |
| 8,292,961 B2 | 10/2012 | Osman | 623/17.12 |
| 8,317,864 B2 | 10/2012 | Kim | 623/17.11 |
| 8,337,556 B2 | 12/2012 | Shaolian et al. | 623/17.12 |
| 8,337,557 B2 | 12/2012 | Collins et al. | 623/17.12 |
| 8,349,013 B2 | 1/2013 | Zucherman et al. | 623/17.12 |
| 8,377,131 B2 | 2/2013 | Lin | 623/17.12 |
| 8,377,136 B2 | 2/2013 | Simonton | 623/17.16 |
| 8,377,138 B2 | 2/2013 | Reo et al. | 623/17.16 |
| 8,382,838 B2 | 2/2013 | Baumgartner et al. | 623/17.12 |
| 8,398,511 B2 | 3/2013 | Sandusky | 473/604 |
| 8,403,987 B2 | 3/2013 | Reo et al. | 623/17.11 |
| 8,419,839 B2 | 4/2013 | Shimatani | 96/12 |
| 8,444,694 B2 | 5/2013 | Collins et al. | 623/17.12 |
| 8,449,660 B2 | 5/2013 | Shimatani et al. | 96/11 |
| 8,454,612 B2 | 6/2013 | Lambrecht et al. | 606/86 R |
| 8,460,383 B2 | 6/2013 | Wirtel, III et al. | 623/17.12 |
| 8,480,718 B2 | 7/2013 | Protopsaltis et al. | 606/331 |
| 8,540,772 B2 | 9/2013 | Osman | 623/17.12 |
| 8,551,172 B2 | 10/2013 | Park | 623/17.12 |
| 8,562,634 B2 | 10/2013 | Middleton | 606/170 |
| 8,603,171 B2 | 12/2013 | McClellan, III et al. | 623/17.16 |
| 8,636,803 B2 * | 1/2014 | Hibri | A61F 2/441 623/17.12 |
| 8,663,328 B2 | 3/2014 | Justis et al. | 623/17.12 |
| 8,690,919 B2 | 4/2014 | Lange et al. | 606/249 |
| 8,727,920 B2 | 5/2014 | Sandusky | 473/603 |
| 8,734,459 B1 | 5/2014 | Alobaid | 606/92 |
| 8,747,475 B2 | 6/2014 | Kuslich | 623/17.16 |
| 8,808,381 B2 | 8/2014 | Kim et al. | 623/17.13 |
| 8,888,850 B2 | 11/2014 | Linares | 623/17.12 |
| 8,894,563 B2 | 11/2014 | Connors et al. | 600/30 |
| 8,945,223 B2 | 2/2015 | Trieu | 623/17.12 |
| 8,979,931 B2 | 3/2015 | Stad et al. | 623/17.12 |
| 2002/0198588 A1 | 12/2002 | Armstrong et al. | 623/1.13 |
| 2003/0028251 A1 | 2/2003 | Mathews | 623/17.16 |
| 2003/0040772 A1 | 2/2003 | Hyodoh et al. | 606/200 |
| 2003/0114917 A1 | 6/2003 | Holloway et al. | 623/1.13 |
| 2005/0015150 A1 | 1/2005 | Lee | 623/17.12 |
| 2005/0137675 A1 | 6/2005 | Dubson et al. | 623/1.4 |
| 2007/0200271 A1 * | 8/2007 | Dave | A61L 31/041 264/211 |
| 2008/0046082 A1 | 2/2008 | Lee | 623/17.16 |
| 2008/0119943 A1 | 5/2008 | Armstrong et al. | 623/23.7 |
| 2008/0195210 A1 | 8/2008 | Milijasevic et al. | 623/17.16 |
| 2009/0012618 A1 | 1/2009 | Ahrens et al. | 623/17.12 |
| 2009/0076609 A1 | 3/2009 | Stewart | 623/17.16 |
| 2009/0076610 A1 | 3/2009 | Afzal | 623/17.16 |
| 2009/0105823 A1 | 4/2009 | Williams et al. | 623/17.16 |
| 2009/0118833 A1 | 5/2009 | Hudgins et al. | 623/17.16 |

(56) References Cited

U.S. PATENT DOCUMENTS

| | | | |
|---|---|---|---|
| 2009/0163994 A1 | 6/2009 | Quigley et al. | 623/1.15 |
| 2009/0299476 A1 | 12/2009 | Diwan et al. | 623/17.12 |
| 2010/0193999 A1 | 8/2010 | Anneaux et al. | 264/438 |
| 2010/0256766 A1 | 10/2010 | Hibri et al. | 623/17.16 |
| 2010/0292798 A1 | 11/2010 | Maestretti | 623/17.12 |
| 2011/0093076 A1 | 4/2011 | Reo et al. | 623/17.16 |
| 2012/0089227 A1 | 4/2012 | Jarzem | 623/17.12 |
| 2012/0165941 A1 | 6/2012 | Rabiner et al. | 623/17.12 |
| 2012/0310352 A1 | 12/2012 | DiMauro et al. | 623/17.16 |
| 2013/0103155 A1 | 4/2013 | Tornier et al. | 623/17.16 |
| 2013/0131806 A1 | 5/2013 | Carpetner | 623/17.12 |
| 2013/0297026 A1 | 11/2013 | de Villiers et al. | 623/17.12 |
| 2014/0052250 A1 | 2/2014 | Wirtel et al. | 623/17.12 |
| 2014/0094914 A1 | 4/2014 | Hibri et al. | 623/17.12 |
| 2014/0277467 A1 | 9/2014 | Hibri et al. | |
| 2014/0288656 A1 | 9/2014 | Kuslich | 623/17.16 |
| 2015/0057752 A1 | 2/2015 | Hibri et al. | 623/17.12 |

FOREIGN PATENT DOCUMENTS

| | | |
|---|---|---|
| WO | WO 2006060482 | 12/2005 |
| WO | WO 2014/158762 | 10/2014 |

OTHER PUBLICATIONS

Office Action issued in Chinese Patent Application No. 201580066464.5, dated Aug. 2, 2018, dated Aug. 22, 2018.

* cited by examiner

PERCUTANEOUS IMPLANTABLE NUCLEAR PROSTHESIS

CROSS-REFERENCE TO RELATED APPLICATIONS

This application claims the benefit of priority of U.S. Provisional Patent Application No. 62/074,925, filed Nov. 4, 2014, which is hereby incorporated by reference in its entirety.

BACKGROUND

1. Field of the Invention

This application relates generally to methods and devices for repairing an intervertebral disc. More specifically, the application relates to a percutaneously deployed implantable disc replacement and methods for manufacturing such a disc replacement/prosthesis.

2. Description of Related Art

A common medical issue is back pain due to spinal disc injuries caused by trauma, the aging process or other disorders. One method of treatment that has been proposed is to remove the existing nucleus pulposus and replace it with a nuclear prosthesis formed in situ using open surgery or minimally invasive surgical techniques. One proposed method comprises the steps of (i) providing a mold, such as a balloon, to contain a flowable curable material that can cure in situ within the disc space, (ii) providing a conduit to connect the mold cavity to a source of flowable curable material, (iii) delivering the flowable curable material into the mold to fill the cavity, and (iv) permitting the curable material to cure.

The existing techniques for forming a nuclear prosthesis in situ have not achieved convincing clinical acceptance or commercial success. One problem identified by the present inventors is the substantial difference in the modulus of elasticity between the vertebral bony elements, including the vertebral end plates, and the annulus fibrosus on the one hand, and the implanted elements on the other. The high modulus of elasticity of the implanted material is disadvantageous since it does not dampen impacts or sudden increases in intradiscal pressure during extreme bending or torsion, especially during high loading peaks. The large difference in the modulus of elasticity between implanted disc materials and adjacent tissues can also lead to softening of the vertebral end plates and adjacent bone (spongeosus), resulting in subsidence of the nuclear implant. Migration and expulsion of the implant can also occur.

Therefore, there is a need for an improved nuclear implant.

SUMMARY

An object of exemplary embodiments of the present invention is to provide a method of manufacturing an elastomeric enclosure for a multi-chamber nuclear implant that can selectively and controllably be inflated and deflated with materials that, together, provide physical and mechanical properties similar to those of a normal disc, and which can be tailored to individual patient parameters.

Another object of exemplary embodiments of the present invention is to provide a method of fabricating a nuclear implant that can be deployed percutaneously in a disc cavity and inflated to conform to the shape and size of the disc cavity.

A further object of exemplary embodiments of the present invention is to provide a nuclear implant which reinforces the annulus fibrosus if it is torn.

According to an exemplary embodiment, an implantable prosthetic device comprises an inner inflatable enclosure having a first opening and an outer inflatable enclosure having a first opening. The outer inflatable enclosure encapsulates the inner inflatable enclosure. A valve assembly sealingly couples the first opening of the outer inflatable enclosure and the first opening of the inner inflatable enclosure, and the valve assembly is configured to allow independent inflation of the outer and inner inflatable enclosures. An annular reinforcement band is provided around the periphery of the outer inflatable enclosure. When implanted, the inner chamber is filled with a compressible material and the outer inflatable enclosure is filled with an in situ curable material, such as silicone. This structure allows for vertical and horizontal load stresses placed on the implant to be redirected inward, centrally toward the inner compressible enclosure instead of outward.

The inner and outer inflatable enclosures may comprise a seamless, unitary piece of material. The inner inflatable enclosure may have a second opening generally opposite of the first opening, the outer inflatable enclosure may have a second opening generally opposite of the first opening, and a plug may sealingly couple the second opening of the inner inflatable enclosure and the second opening of the outer inflatable enclosure. The plug may be coupled to a neck portion of the second opening of the outer inflatable enclosure. The plug and the neck portion of the second opening of the outer inflatable enclosure may be coupled to a neck portion of the second opening of the inner inflatable enclosure.

The annular reinforcement band may be placed into the second opening of the inner inflatable enclosure and then the distal plug may be inserted into the second opening to couple the reinforcement band to the balloon. The reinforcement band may be coupled to the inflatable enclosure at only one location, such as at the plug. A fastener may be provided to fasten the reinforcement band to the plug. The reinforcement band may include a shape memory material. The annular reinforcement band may comprise a tubular braid enclosing the shape memory material.

The valve assembly may comprise a valve core coupling the first openings of the outer and inner inflatable enclosures. The valve core has an opening from an interior of the valve core to an exterior of the valve core. A valve membrane partially envelops the valve core and has an opening into the outer inflatable enclosure. The opening in the valve membrane and the valve core are separated from one another to allow material to flow into the outer inflatable enclosure, while preventing backflow. The valve core may further comprise a resealable, puncturable membrane to provide access to the inner inflatable enclosure.

The valve membrane and the valve core may be integrally molded, or the valve core may be bonded to the valve membrane with an adhesive.

The inner and outer inflatable enclosures may comprise an elastomer, such as silicone rubber.

In some embodiments, a curable material may be provided to inflate the outer inflatable enclosure, and a compressible material such as gas may be provided to inflate the inner inflatable enclosure to allow the cured material to deform. The cured material may substantially surround the inner inflatable enclosure. In other embodiments, an incompressible material (e.g., a liquid) is provided to inflate the inner inflatable enclosure and then the curable material is injected into the outer inflatable enclosure. The incompressible material is then removed from the inner inflatable enclosure and replaced with a compressible material (e.g., a gas). In certain embodiments, the curable material further polymerizes with the inner and outer inflatable enclosures to form a solid, unitary member.

In accordance with an exemplary embodiment, a valve assembly for inflating an implantable prosthetic device comprising an inner inflatable enclosure connected to an outer inflatable enclosure comprises an elastomeric membrane forming a passageway from an interior of the inner inflatable enclosure to an exterior of the outer inflatable enclosure and a valve core disposed in the passageway so that the elastomeric membrane surrounds the valve core. The elastomeric membrane has an opening into an interior of the outer inflatable enclosure, and the elastomeric membrane surrounds the valve core. The valve core comprises a conduit extending from a first end to a second end, and a resealable, puncturable membrane at the second end of the valve core conduit for providing resealable access to the inner inflatable enclosure. An opening in the conduit extends from an interior of the conduit to an exterior of the conduit, and the opening in the valve core is offset from the opening in the elastomeric membrane to form a one way valve allowing material introduced into the interior of the conduit to pass into the interior of the outer inflatable enclosure while preventing backflow.

In accordance with an exemplary embodiment, a method of implanting a prosthetic device into an intervertebral space having a nucleus pulposus surrounded by an annulus fibrosus comprises penetrating the annulus fibrosus, removing the nucleus pulposus, and implanting an implantable prosthetic device, wherein the implantable prosthetic device comprises an inner inflatable enclosure having a first opening and an outer inflatable enclosure having a first opening. The outer inflatable enclosure encapsulates the inner inflatable enclosure. A valve assembly sealingly couples the first opening of the outer inflatable enclosure and the first opening of the inner inflatable enclosure, and the valve assembly is configured to allow independent inflation of the outer and inner inflatable enclosures. A reinforcement band is provided around the periphery of the outer inflatable enclosure.

In some embodiments, the method may further comprise inflating the inner inflatable enclosure using a compressible material, and the compressible material may comprise a gas. The method may further comprise inflating the outer inflatable enclosure using a curable material, and the curable material may be silicone rubber. In other embodiments, the method may further comprise inflating the inner inflatable enclosure using an incompressible material, and the incompressible material may comprise a liquid. The method may further comprise inflating the outer inflatable enclosure using a curable material, allowing the curable material to cure, and then replacing the incompressible material in the inner inflatable enclosure with a compressible material.

In accordance with an exemplary embodiment, a method of producing an implantable prosthetic device comprises (i) injection molding a prosthesis blank comprising an outer membrane section with a proximal end and a distal end, an inner membrane section with a proximal end and a distal end, a valve section disposed between the proximal end of the outer membrane section and the proximal end of the inner membrane section, a distal plug inner section at the distal end of the inner membrane section, and a distal plug outer section at the distal end of the outer membrane section; and (ii) partially inverting the prosthesis blank so that the outer membrane section encloses the inner membrane section to form an outer balloon surrounding an inner balloon formed by the inner membrane.

In accordance with an exemplary embodiment, a method of producing an implantable prosthetic device comprises (i) providing a mandrel with a profiled outer surface configured to form a prosthesis blank comprising an outer membrane section with a proximal end and a distal end, an inner membrane section with a proximal end and a distal end, a valve section disposed between the proximal end of the outer membrane section and the proximal end of the inner membrane section, a distal plug inner section at the distal end of the inner membrane section, and a distal plug outer section at the distal end of the outer membrane section; (ii) coating the mandrel with a material to form the prosthesis blank; (iii) stripping the prosthesis blank from the mandrel; and (iv) partially inverting the prosthesis blank so that the outer membrane section encloses the inner membrane section to form an outer balloon surrounding an inner balloon formed by the inner membrane.

The mandrel may comprise a unitary body, and the valve section of the mandrel may comprise a valve core that is integrally molded with the prosthesis blank. The mandrel may comprise two separable pieces coupled to the valve core, and the step of stripping the prosthesis blank from the mandrel may comprise separating the mandrel pieces from the valve core and removing the separable pieces from the prosthesis blank.

The valve core may be glued into the valve section.

The distal plug may be inserted into the distal plug outer section to seal the distal plug outer section, and the distal plug and distal plug outer section may be inserted into the distal plug inner section.

A reinforcing band may be joined to the distal plug, and the reinforcing band, distal plug, and distal plug outer section may be inserted into the distal plug inner section. The reinforcing band may be joined to the distal plug with a fastener.

The mandrel may be coated by dipping it into a polymer liquid, which may comprise a silicone dispersion, and dried.

The elastomeric membrane may be stripped from the mandrel by melting the mandrel, or the prosthesis blank may be removed from the mandrel by stretching it over the mandrel. A reinforcing band may be applied around the periphery of the outer balloon.

In accordance with an exemplary embodiment, a mandrel for producing an implantable prosthetic device comprises a first balloon mandrel with a profiled outer surface configured in the shape of a first balloon; a second balloon mandrel with a profiled outer surface configured in the shape of a second balloon; and a valve core disposed between the first and second balloon mandrels. The outer surface of the first balloon mandrel may further comprises a distal opening section, and the outer surface of the second balloon mandrel may further comprise a distal opening section. The outer surfaces of the balloon mandrels may be curved. The outer surfaces of each of the balloon mandrels may comprise a central section with a generally uniform diameter.

In accordance with an exemplary embodiment, a mandrel for producing an implantable prosthetic device comprises a unitary body with a profiled outer surface. The profiled outer surface has an outer membrane section configured to form an annular balloon with a proximal end and a distal end; an inner membrane section configured to form a nuclear balloon with a proximal end and a distal end; a valve section configured to receive a valve assembly disposed between the proximal end of the outer membrane section and the proximal end of the inner membrane section; a distal plug outer section configured to receive a distal plug at the distal end of the outer membrane section; and a distal plug inner section configured to receive an assembly of the distal plug and distal plug outer section at the distal end of the inner membrane section.

The term "coupled" is defined as connected, although not necessarily directly. The terms "a" and "an" are defined as one or more unless this disclosure explicitly requires otherwise. The terms "substantially," "approximately," and "about" are defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

A device, system, or component of either that is configured in a certain way is configured in at least that way, but it can also be configured in other ways than those specifically described.

Any embodiment of any of the systems and methods can consist of or consist essentially of—rather than comprise/include/contain/have—any of the described elements, features, and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are presented below.

DETAILED DESCRIPTION

Figure 1:
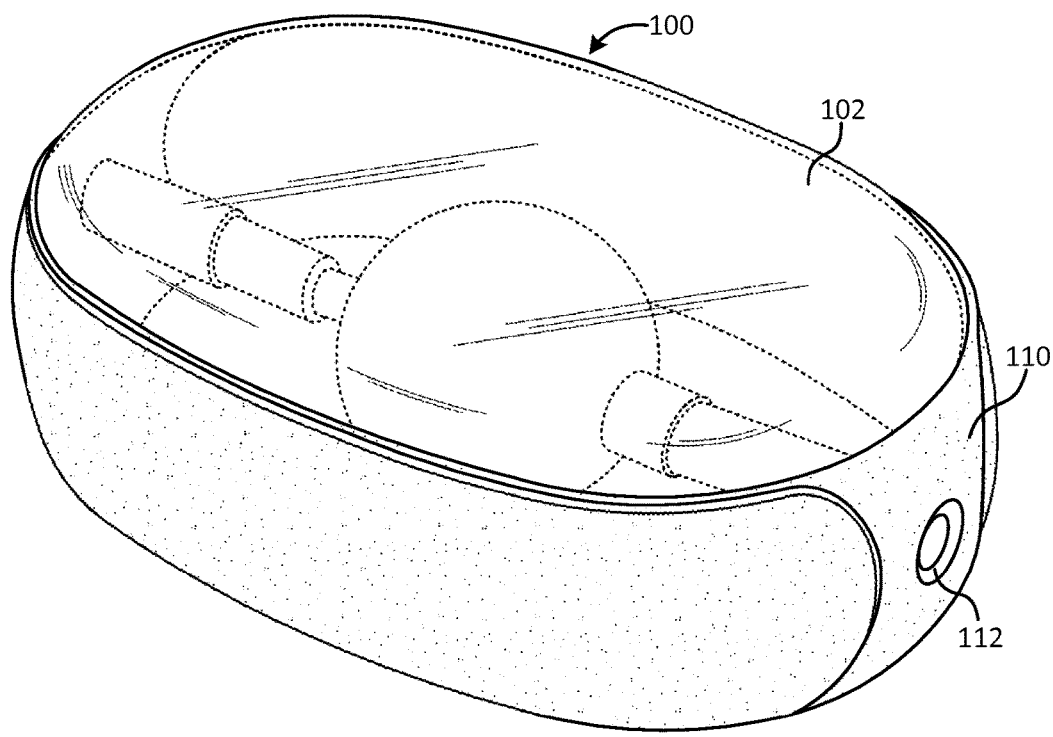
FIG. 1 is a perspective view of an inflated implant in accordance with an embodiment of the present invention.
Figure 2:
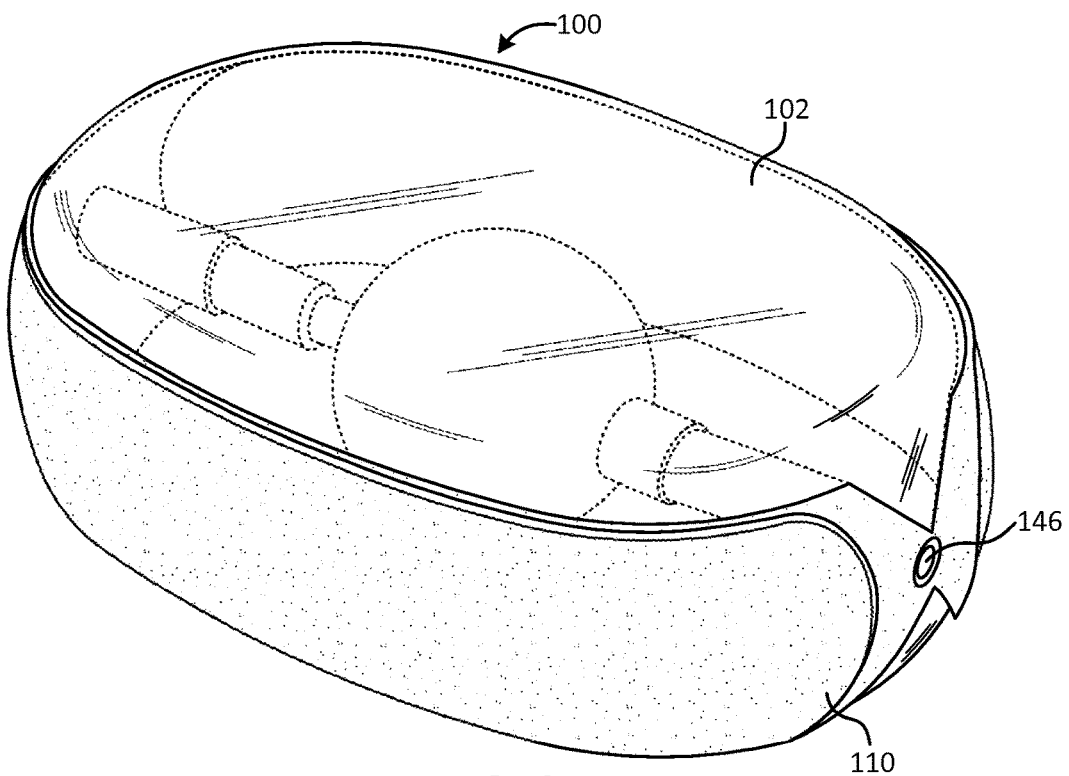
FIG. 2 is a perspective view of the inflated implant of FIG. 1 from another direction.
Figure 3:
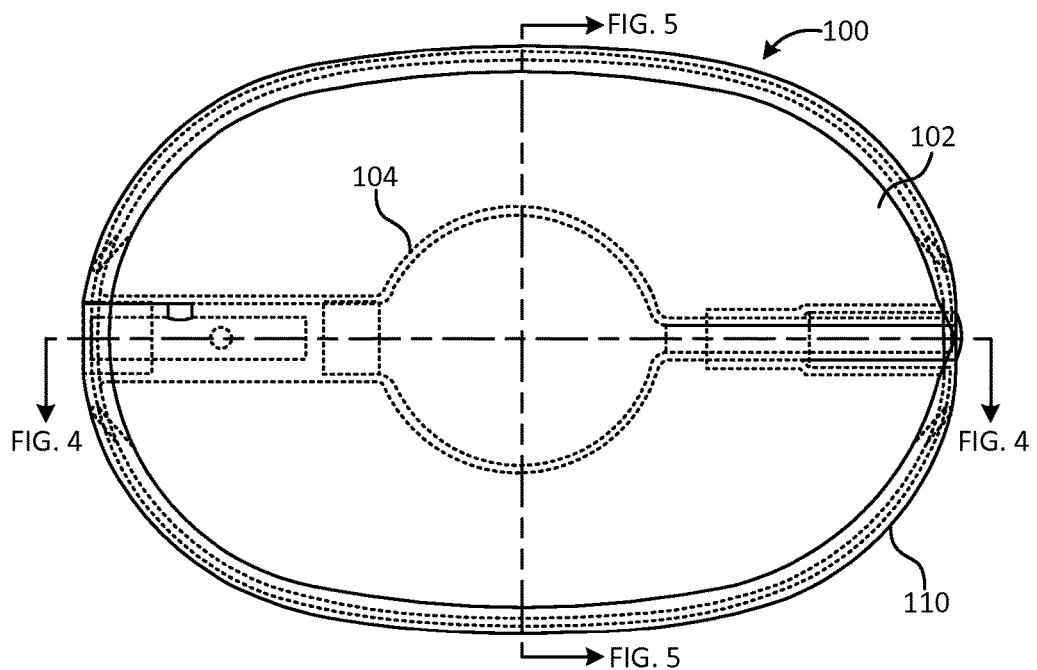
FIG. 3 is a top view of the implant of FIG. 1.
Figure 4:
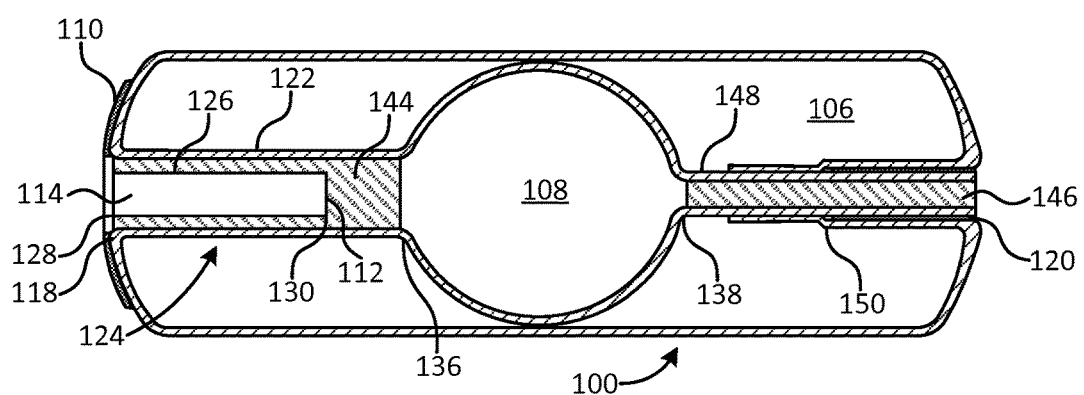
FIG. 4 is a sectional view taken through line 4-4 in FIG. 2.
Figure 5:
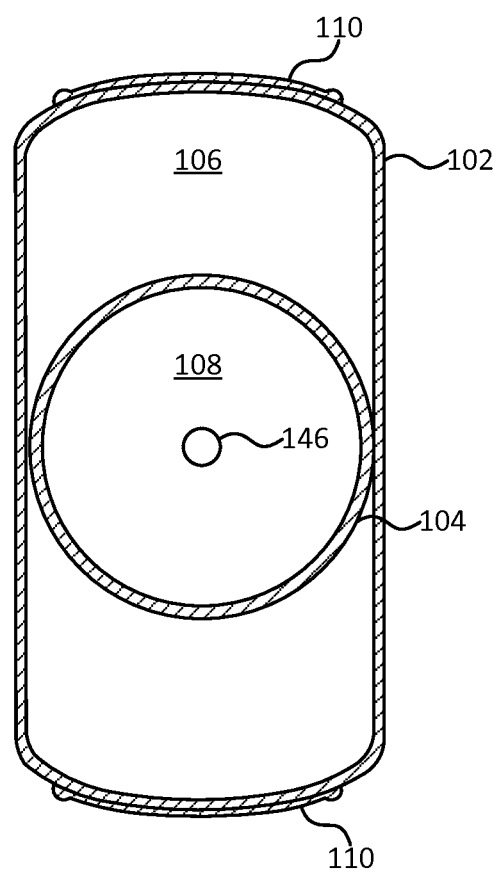
FIG. 5 is a sectional view taken through line 5-5 in FIG. 2.
Figure 6:
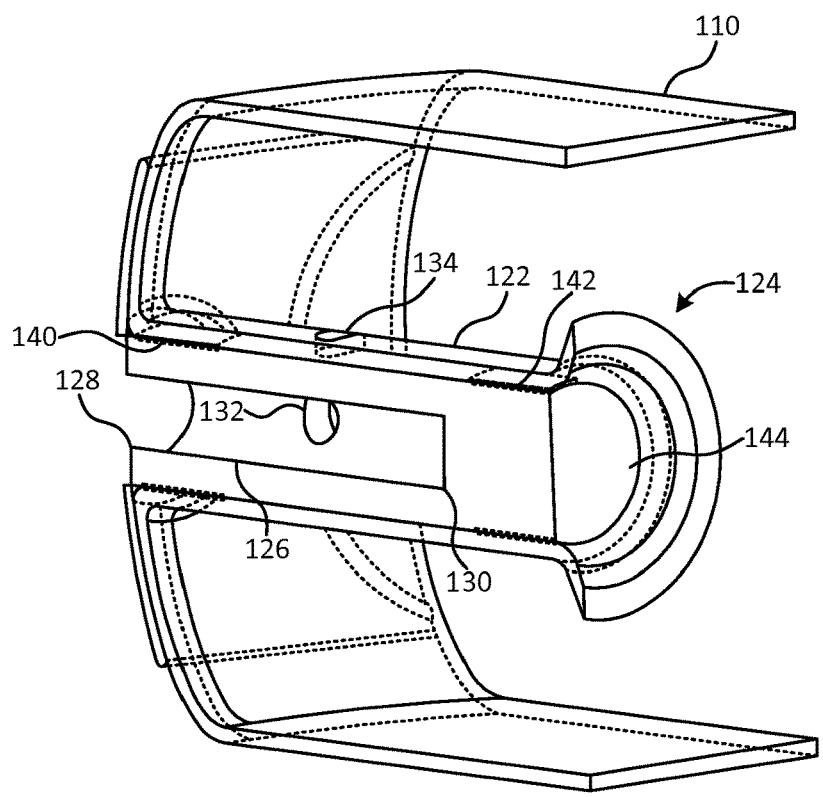
FIG. 6 is a cut-away view of a portion of an implant valve of the implant of FIG. 1.
Figure 7:
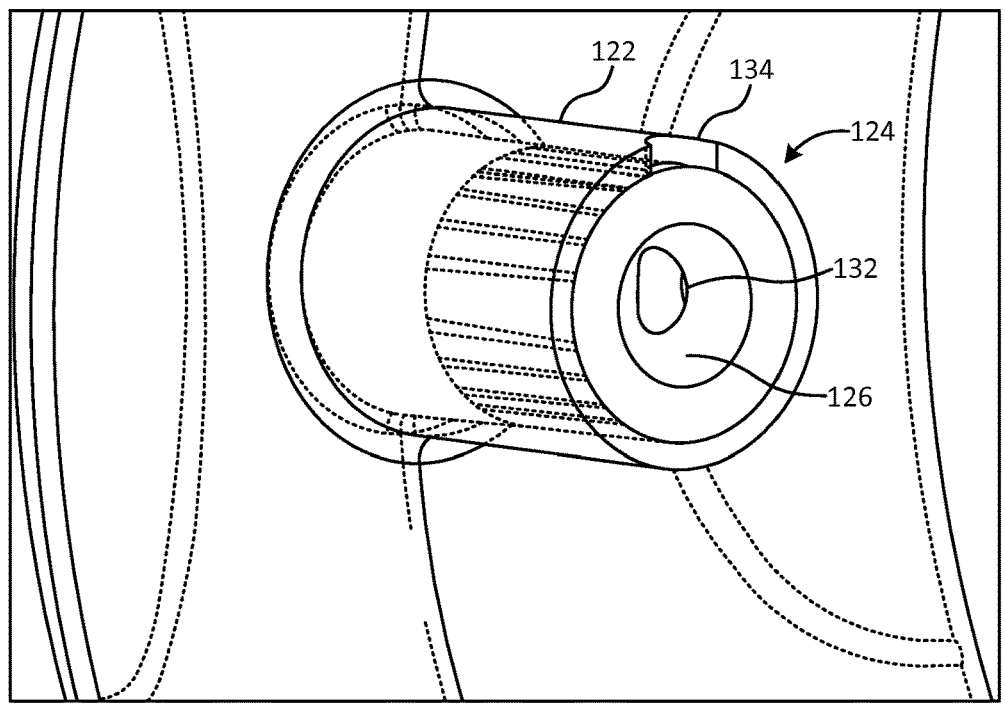
FIG. 7 is a cut-away view of a portion of the implant valve of FIG. 6.
Figure 8:
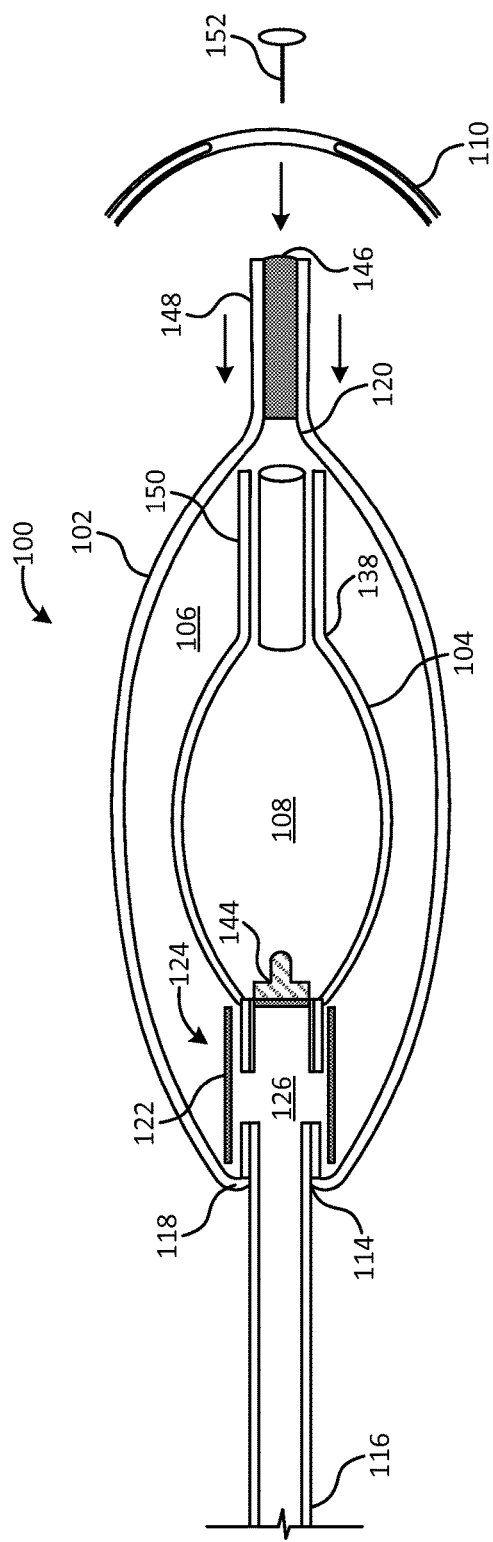
FIG. 8 is a sectional view of an implant assembly prior to insertion of a distal plug and attachment of an annular reinforcing member.

In the following detailed description, reference is made to the accompanying drawings, in which are shown exemplary but non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. In the accompanying drawings, like reference numerals refer to like parts throughout the various figures unless otherwise specified.

Description of Implant

Referring to FIGS. 1-8, an embodiment of a percutaneously deliverable spinal implant 100 includes an outer inflatable enclosure (or balloon) 102 and an inner inflatable enclosure (or balloon) 104. Outer inflatable enclosure 102 forms an annular chamber 106, and inner inflatable enclosure 104 forms a nuclear chamber 108. Nuclear chamber 108 is encapsulated within annular chamber 106. Preferably, outer and inner inflatable enclosures 102, 104 are formed as a seamless, unitary piece of an elastomeric material, such as silicone rubber. The use of an elastomeric material produces compliant outer and inner balloons 102, 104. That is, the outer and inner balloons 102, 104 expand when internal pressure is applied. The use of compliant balloons provides certain advantages. Compliant balloons accommodate the irregular, flat or discoid configuration of the nuclear space. Furthermore, a compliant balloon maintains an appropriate modulus of elasticity of the nuclear implant following elastomeric curing, and preserve bio-mechanical mobility of the vertebral segment, and allows unhindered deformation of the cured silicone component into the central void.

An annular reinforcing band 110 may be disposed around the perimeter of the lateral edges of implant 100 to minimize or prevent over-stretching of the elastomeric membrane or over inflation of outer and inner balloons 102, 104 circumferentially. Annular reinforcement band 110 encourages vertical expansion to widen the disc space. The vertebral superior and inferior end plates constrain the expansion of the implant 100.

The size of implant 100 is selected so that it can be percutaneously inserted into a denucleated intervertebral disc space while deflated and then inflated to fill the denucleated cavity. In one embodiment, the exterior of inflated implant 100 is approximately 30 mm in length, 20 mm in width, and 10 mm in height, and the exterior of inner inflatable enclosure 104 is approximately 9 mm long, 6 mm wide, and 6 mm thick.

Annular reinforcing band 110 may be a biocompatible textile material. In one embodiment, annular reinforcing band 110 comprises a tubular, woven textile material. Annular reinforcing band 110 may also include an expandable member to provide additional support. The expandable member may be formed of a shape memory material, such as nitinol. U.S. Pat. No. 8,636,803, entitled Percutaneous Implantable Nuclear Implant, discloses one suitable construction of annular reinforcing band 110, and is hereby incorporated by reference in its entirety for all purposes.

Outer inflatable enclosure 102 has a first opening 118 and a second opening 120. Inner inflatable enclosure 104 has a first opening 136 and a second opening 138. A proximal plug, or valve core, 112 connects first opening 118 and first opening 136. A valve membrane 122 surrounds proximal plug 112 and cooperates with proximal plug 112 to form an inflation valve 124. Inflation valve 124 is a one-way valve which allows material to be introduced into annular chamber 106. Preferably, valve membrane 122 is formed integrally with outer and inner inflatable enclosures 102, 104, as will be described in further detail below. As seen most clearly in FIGS. 6-8, proximal plug 112 comprises a conduit 126 extending from a first end 128 to a second end 130. First end 128 of proximal plug 112 forms a port 114 for receiving an inflation stylus 116. Valve membrane 122 is coupled to proximal plug 112 by first and second adhesive bands 140, 142, which are substantially fluid tight. The portion of valve membrane 122 between first and second adhesive bands 140, 142 is unbonded to form a channel for allowing material to flow therethrough. At least one opening 132 extends from conduit 126 to the exterior of proximal plug 112. Valve membrane 122 has at least one opening 134 which is offset from opening 132. In this manner, when a suitable material (described in detail below) is introduced into conduit 126 under pressure, the material is introduced through opening 132 into annular chamber 106, stretches valve membrane 122, and flows out through opening 134. When pressure is removed from conduit 126, valve membrane 122 seals opening 132 and prevents backflow through opening 132. Second end 130 of conduit 126 is closed by a puncturable, resealable membrane 144.

Figure 9:
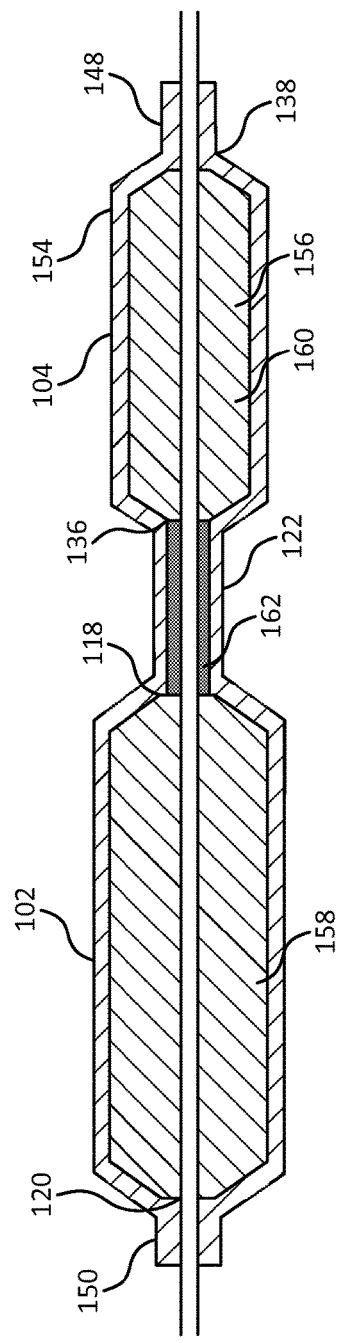
FIG. 9 is a sectional view of a mandrel and implant according to an embodiment of the present invention.
Figure 10:
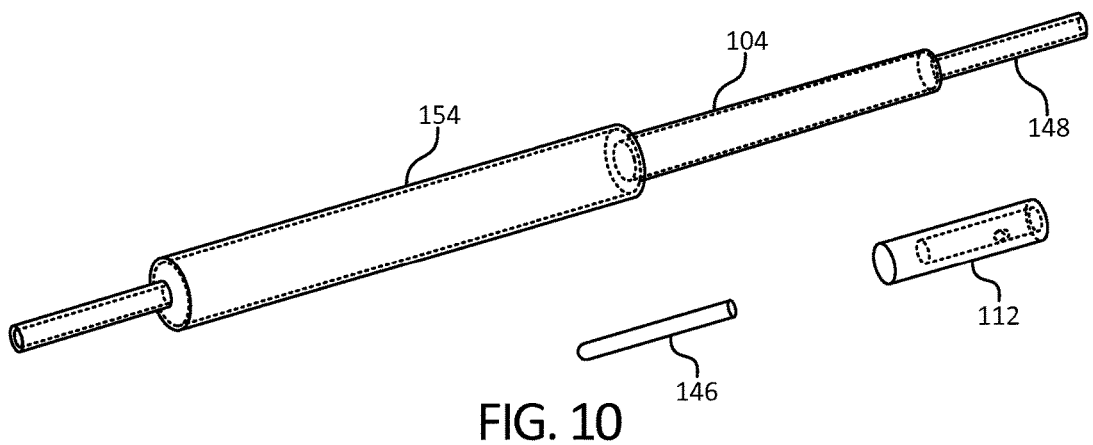
FIG. 10 illustrates a first assembly step for the implant assembly of FIG. 1.
Figure 11:
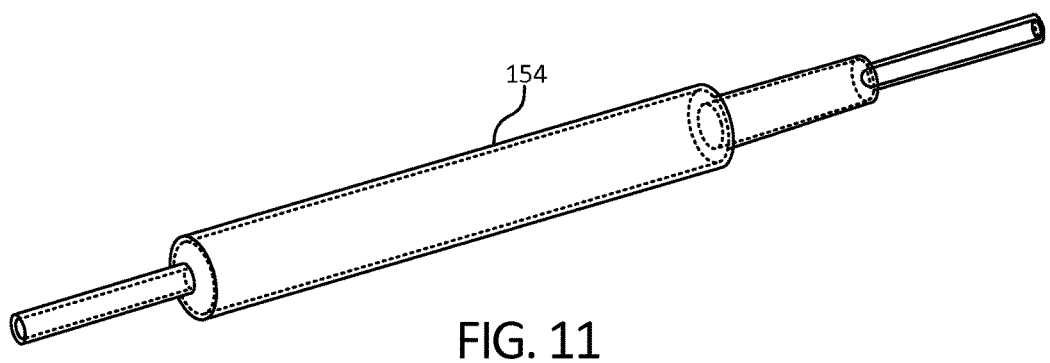
FIG. 11 illustrates a second assembly step for the implant assembly of FIG. 1.
Figure 12:
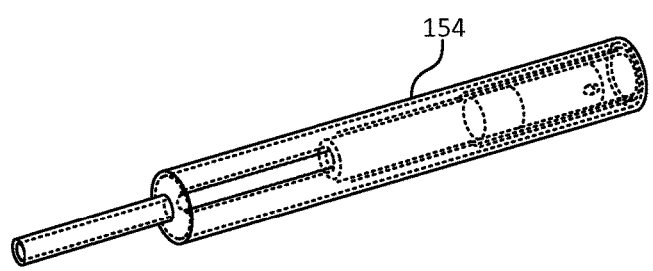
FIG. 12 illustrates a third assembly step for the implant assembly of FIG. 1.

A distal plug 146 is disposed in a neck portion 148 extending from second opening 138 of the inner inflatable enclosure 104. The distal plug 148 is bonded to the neck portion 148 to form a fluid tight seal. The distal plug 146 and neck portion 148 assembly is disposed within a neck portion 150 extending from second opening 120 of outer inflatable enclosure 102. Annular reinforcing band 110 may be trapped between the distal plug 146 and neck portion 148 assembly and the neck portion 150 to serve as an anchor for reinforcing band 110. Alternatively, a fastener 152 may be used to anchor annular reinforcing band 110 to distal plug 146, as seen most clearly in FIG. 9.

Method of Manufacturing the Implant

Referring to FIGS. 9-13, in one embodiment, inner and outer inflatable enclosures 102, 104 are formed from a unitary implant blank 154. Implant blank 154 may be produced by dip molding using a mandrel 156. Mandrel 156 comprises an outer membrane section 158, an inner membrane section 160, and a valve section 162. Mandrel 156 may be one piece or multiple pieces. In one embodiment, outer membrane section 158, inner membrane section 160, and valve section 162 are separate pieces which are assembled together. Mandrel 156 is dipped into a polymer liquid, such as a silicone dispersion, removed from the liquid and allowed to dry or cure. Mandrel 156 may be dipped one or more times to build up a desired thickness of material. The blank 154 comprises neck portion 150, outer inflatable enclosure 102, valve membrane 122, inner inflatable enclosure 104, and neck portion 148.

After curing or drying, implant blank 154 is stripped from mandrel 156. This may be accomplished by stretching implant blank 154 over mandrel 156. If mandrel 156 is composed of separable pieces, it may be disassembled prior to stripping. In one embodiment, mandrel 156 may be formed of a meltable or dissolvable material and melted or dissolved to strip implant blank 154 from mandrel 156. Opening 134 through valve membrane 122 is formed in implant blank 154.

Figure 13:
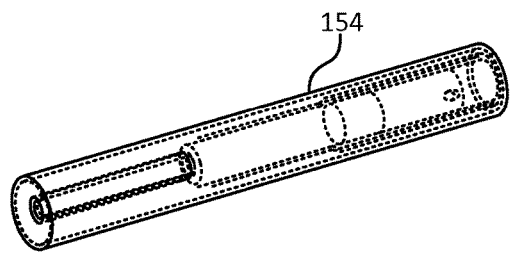
FIG. 13 illustrates a fourth assembly step for the implant assembly of FIG. 1.
Figure 14:
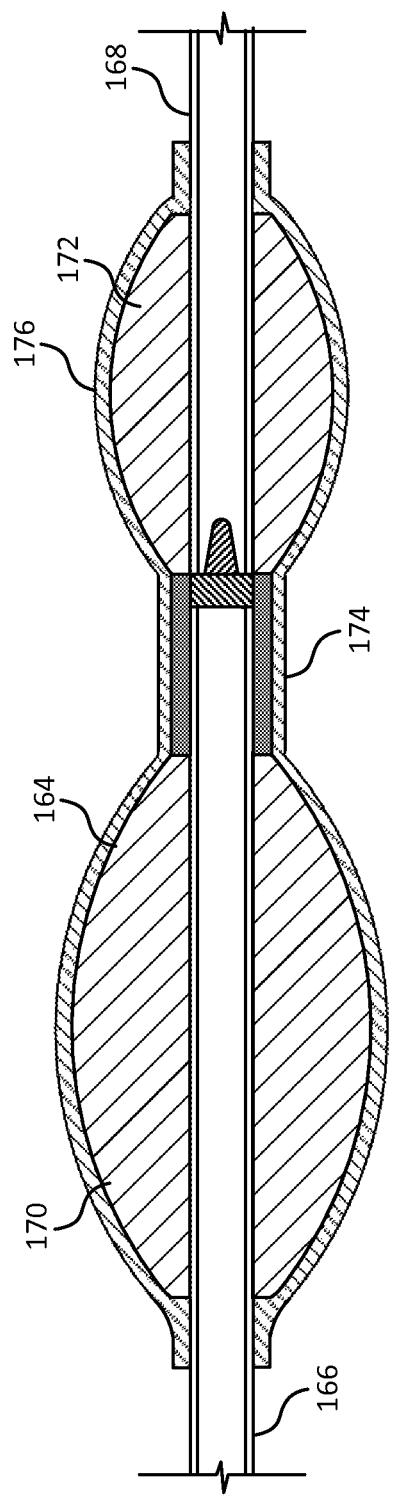
FIG. 14 is a sectional view of a mandrel and implant assembly according to another embodiment of the present invention.

Referring to FIGS. 10-13, implant blank 154, distal plug 146 and proximal plug (or valve core) 112 are provided. Neck portion 148 which extends from inner inflatable enclosure 104 is inverted into the interior of inner inflatable enclosure 104 and distal plug 146 is inserted into neck portion 148 and glued into place. The neck portion is the further inverted into the annular chamber 106. Next, proximal plug 112 is inserted and glued into the valve membrane 122. This is done in two steps. First, the end of proximal plug 112 nearest the annular chamber 106 is glued to valve membrane 122 with first adhesive band 142. Next, the implant blank 154 is further inverted, and second adhesive band 142 is applied to glue implant blank 154 to the second end of proximal plug 112. This results in the configuration shown in FIG. 12. Next, neck portion 150 is tucked into outer inflatable enclosure 102 (as indicated by the arrows in FIG. 8) and over distal plug 146 and neck portion 148, as shown in FIG. 13. Annular reinforcing band 110 may be tucked in at the same time, or may be fastened to distal plug 146 by a fastener.

In another embodiment, implant blank 154 is formed by injection molding over a mandrel using conventional techniques. That is, the mandrel is placed into an injection mold having a cavity corresponding to the outer shape of the implant blank, and a curable material is injected into the mold under pressure. The curable material is allowed to cure, thereby forming implant blank 154 over the mandrel. The mandrel and implant blank 154 are then removed from the injection mold. Once implant blank 154 is formed, the remaining assembly steps are as described in the prior paragraph.

Figure 15:
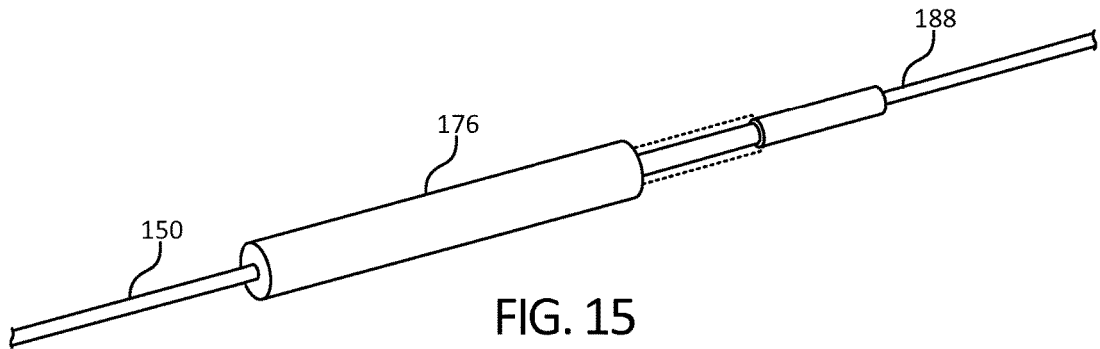
FIG. 15 illustrates a first assembly step for the implant assembly of FIG. 1.
Figure 16:
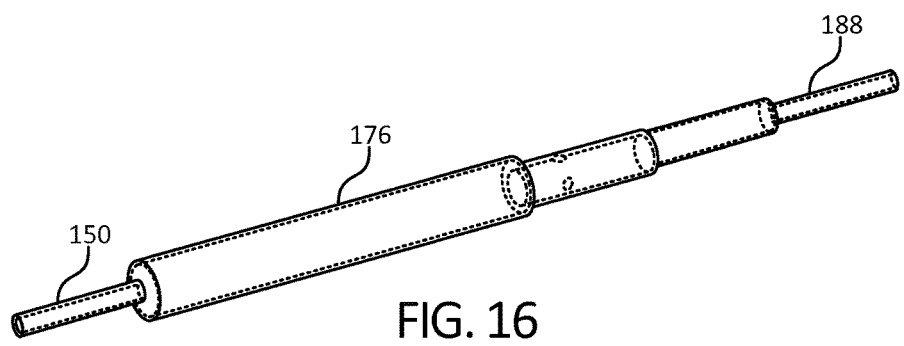
FIG. 16 illustrates a second assembly step for the implant assembly of FIG. 1.
Figure 17:
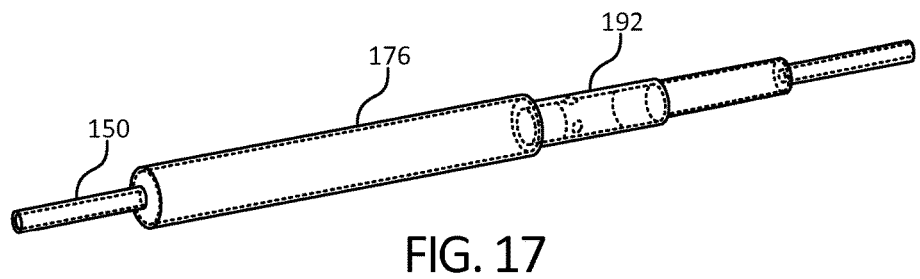
FIG. 17 illustrates a third assembly step for the implant assembly of FIG. 1.
Figure 18:
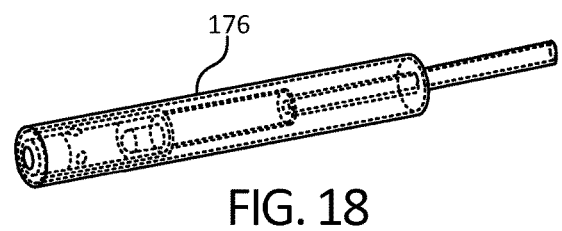
FIG. 18 illustrates a fourth assembly step for the implant assembly of FIG. 1.
Figure 19:
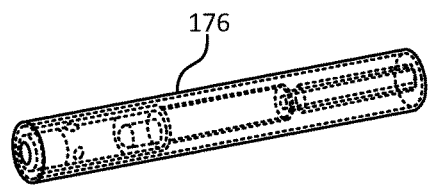
FIG. 19 illustrates a final assembly step for the implant assembly of FIG. 1.

FIGS. 14-19 illustrate another method of making an implant 100. In this embodiment, a mandrel 164 comprises a first mandrel section 166 forming an outer membrane section 168 and a second mandrel section 168 forming an inner membrane section 170. First mandrel section 166 is inserted into valve core (or proximal plug) 112, and second mandrel section is mated with the other end of proximal plug 112. Referring to FIG. 15, the mandrel and valve assembly is then dip molded to form an implant blank 176. Referring to FIG. 16, the neck portion 188 of the implant blank 176 is inverted and a proximal plug is glued into the neck portion 188. A valve membrane 192 is applied over the plug section and adhered to the plug section with first and second adhesive bands to form an implant valve. The implant blank 176 is then inverted left to right over the valve core 112, as shown in FIG. 18. Finally, the neck portion 190 tucked into the outer inflatable enclosure 102. Annular reinforcing band 110 may be tucked in at the same time, or may be fastened to distal plug 146 by a fastener.

Method of Deploying an Implant

Referring to FIGS. 20-23, the inflatable implant 100 is particularly well suited for deployment using minimally invasive or percutaneous surgical techniques. To prepare the inflatable implant 100 for deployment, the implant is deflated and stretched to minimize its cross-sectional profile. An insertion stylus 116 is detachably inserted into port 114, then the implant 100 is inserted into a deployment cannula 180. Deployment cannula 180 has a minimal cross-sectional profile.

Figure 20:
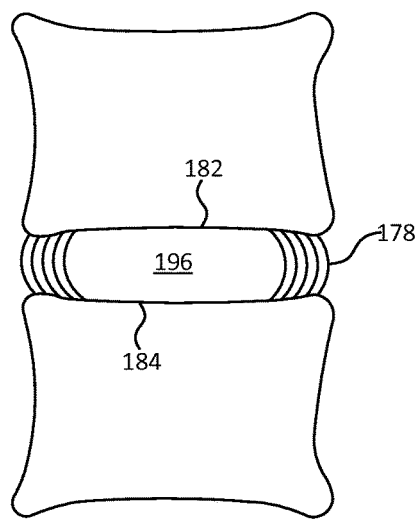
FIG. 20 illustrates a first step in implanting the implant assembly of FIG. 1.

Referring to FIG. 20, to implant the inflatable implant 100, the existing nucleus pulposus is removed by performing a discectomy while leaving the annulus fibrosus 178 substantially intact. Preferably, the discectomy is performed using minimally invasive surgical techniques, such as percutaneous techniques, which leaves a small opening through the annulus fibrosus 178. Once the nucleus pulposus has been removed, the annulus fibrosus 178 and vertebral end plates 182, 184 form a substantially empty disc cavity 182.

Figure 21:
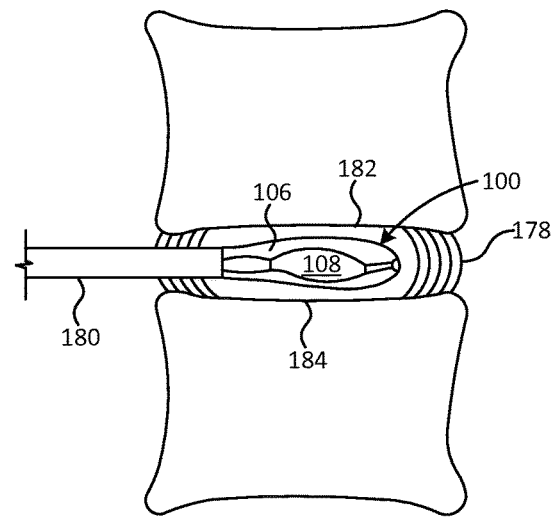
FIG. 21 illustrates a second step in implanting the implant assembly of FIG. 1.

After the nucleus pulposus has been removed, deployment cannula 180 with preloaded implant 100 is placed into the empty disc cavity 182. The implant 100 is deployed by pushing it out of the deployment cannula and into the empty disc cavity, as shown in FIG. 21. The implant 100 is in an uninflated state.

In one embodiment, nuclear chamber 108 is first inflated with a compressible fluid 194, such as a gas. This may be performed using a needle (not shown) which is delivered through the inflation stylus 116 and pushed through the puncturable, resealable membrane 144. The compressible fluid is deployed into the nuclear chamber 108 to inflate the inner inflatable enclosure 104. The pressure of the nuclear chamber 108 is selected so that it provides a buffer zone for inward deformation of the cured elastomer 186 during weight bearing and spine movement. Once nuclear chamber 108 is inflated to the desired pressure, the needle is withdrawn from nuclear chamber 108. In another embodiment, instead of using a removable needle, inflation stylus 116 may have a septum extending through the stylus to divide the stylus into two lumens. One lumen extends through resealable, puncturable membrane 144 into nuclear chamber 108, while the other lumen delivers an in situ curable material to implant valve 124 and annular chamber 106.

Figure 22:
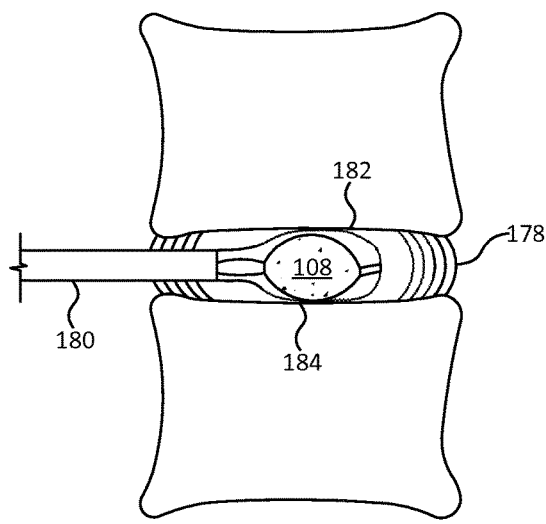
FIG. 22 illustrates a third step in implanting the implant assembly of FIG. 1.
Figure 23:
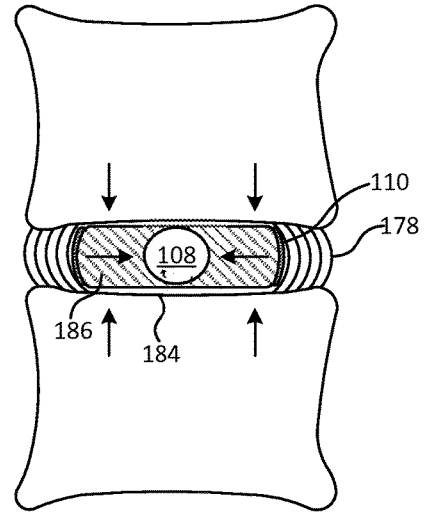
FIG. 23 illustrates a fourth step in implanting the implant assembly of FIG. 1.

Inflation stylus 116 is used to deliver an in situ curable material to annular chamber 106 through the one way implant valve 124 (FIG. 22). The curable material is preferably an elastomeric material, such as silicone rubber, which further polymerizes with the material of inner and outer inflatable enclosures 102, 104 to form a unitary member. The modulus of elasticity and other characteristics of the curable material can be selected based upon patient specific parameters. For instance, younger, more active patients may require a firmer material than less mobile geriatric patients. Once annular chamber 106 is inflated to a desired pressure, inflation stylus 116 can be removed. Implant valve 124 prevents the curable material from leaking out of the annular chamber 106.

After the curable material is allowed to cured, the implant 100 comprises an annular ring of a cured elastomer 186 surrounding nuclear chamber 108 which is filled with a compressible material 194. This structure allows for vertical and horizontal load stresses placed on the intervertebral disc space to be redirected inward, centrally toward nuclear chamber 108 (see direction arrows of FIG. 23) instead of outward. Moreover, annular reinforcing band 110 encourages tissue in-growth of native annulus fibrosus 178, thereby providing reinforcement to native annulus fibrosus 178.

In another embodiment, nuclear chamber 108 is first inflated with an incompressible fluid, such as a liquid. This may be performed using a needle or an inflation stylus, as described above. Once nuclear chamber 194 is inflated, inflation stylus 116 is used to deliver an in situ curable material to annular chamber 106 through the one way implant valve 124. After the curable material is allowed to cured, the incompressible fluid is removed from nuclear chamber 108 and replaced with compressible material 194. This may be accomplished with a needle using implant valve 124.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted (e.g., threads may be substituted with press-fittings or welds). Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method of producing an implantable prosthetic device comprising:
    forming a prosthesis blank comprising:
        an outer membrane section with a proximal end and a distal end,
        an inner membrane section with a proximal end and a distal end,
        a valve section disposed between the proximal end of the outer membrane section and the proximal end of the inner membrane section, wherein the valve section comprises a conduit having a sidewall with at least one opening extending through the sidewall;

a distal plug inner section at the distal end of the inner membrane section, and a distal plug outer section at the distal end of the outer membrane section; and partially inverting the prosthesis blank so that the outer membrane section encloses the inner membrane section so that the outer membrane section forms an outer balloon surrounding an inner balloon formed by the inner membrane section.

2. The method of claim 1, further comprising:

providing a mandrel with a profiled outer surface configured to form the prosthesis blank;

coating the mandrel with a material to form the prosthesis blank; and stripping the prosthesis blank from the mandrel.

3. The method of claim 2, wherein the mandrel comprises two separable pieces coupled to a valve core.

4. The method of claim 3, wherein the valve core is integrally molded with the prosthesis blank.

5. The method of claim 4, wherein the step of stripping the prosthesis blank from the mandrel comprises separating the mandrel pieces from the valve core and removing the separable pieces from the prosthesis blank.

6. The method of claim 2, wherein coating the mandrel comprises dipping the mandrel into a polymer liquid.

7. The method of claim 2, wherein stripping the prosthesis blank from the mandrel comprises removing the material coating the mandrel.

8. The method of claim 1, further comprising inserting a distal plug into the distal plug outer section to seal the distal plug outer section.

9. The method of claim 8, further comprising:

joining a reinforcing band to the distal plug;

inserting the reinforcing band, distal plug, and distal plug outer section into the distal plug inner section.

10. The method of claim 9, wherein the reinforcing band is joined to the distal plug with a fastener.

11. The method of claim 8, further comprising inserting the distal plug and distal plug outer section into the distal plug inner section.

12. The method of claim 1, wherein the prosthesis blank is formed by injection molding.

13. The method of claim 1, further comprising gluing a valve core into the valve section.

14. The method of claim 1, further comprising applying a reinforcing band around the periphery of the outer balloon.

* * * * *